(12) United States Patent
Viswanathan

(10) Patent No.: US 6,968,846 B2
(45) Date of Patent: Nov. 29, 2005

(54) METHOD AND APPARATUS FOR REFINABLY ACCURATE LOCALIZATION OF DEVICES AND INSTRUMENTS IN SCATTERING ENVIRONMENTS

(75) Inventor: Raju R. Viswanathan, Clayton, MO (US)

(73) Assignee: Stereotaxis, Inc., St. Louis, MO (US)

( * ) Notice: Subject to any disclaimer, the term of this patent is extended or adjusted under 35 U.S.C. 154(b) by 275 days.

(21) Appl. No.: 10/093,367

(22) Filed: Mar. 7, 2002

(65) Prior Publication Data

US 2003/0171673 A1 Sep. 11, 2003

(51) Int. Cl.[7] .............................................. A61B 19/00
(52) U.S. Cl. ...................................... 128/899; 73/1.79
(58) Field of Search ................ 128/899; 600/407–471; 324/424; 73/1.79

(56) References Cited

U.S. PATENT DOCUMENTS

| | | | |
|---|---|---|---|
| 4,737,794 A | 4/1988 | Jones | 342/448 |
| 4,829,250 A * | 5/1989 | Rotier | 324/225 |
| 5,211,165 A * | 5/1993 | Dumoulin et al. | 600/410 |
| 5,307,072 A | 4/1994 | Jones, Jr. | 342/147 |
| 5,347,289 A * | 9/1994 | Elhardt | 342/448 |
| 5,558,091 A | 9/1996 | Acker et al. | 600/424 |
| 5,592,939 A * | 1/1997 | Martinelli | 600/424 |
| 6,073,043 A | 6/2000 | Schneider | 600/424 |
| 6,172,499 B1 * | 1/2001 | Ashe | 324/207.12 |
| 6,493,573 B1 * | 12/2002 | Martinelli et al. | 600/424 |
| 6,528,989 B1 * | 3/2003 | Hansen | 324/207.12 |

* cited by examiner

Primary Examiner—Francis J. Jaworski
(74) Attorney, Agent, or Firm—Harness Dickey & Pierce PLC

(57) ABSTRACT

A method of localizing a device, medical or otherwise, within a three dimensional environment, the method comprising: (a) transmitting time varying magnetic fields from at least three transmitters, (b) receiving the transmitted electromagnetic radiation as induced voltage signals from at least one receiver mounted on or within said device, and (c) a processing scheme for processing said received voltage signals in order to extract position and orientation localization information for said device, said processing scheme including correction for conducting materials in the vicinity by the use of information gathered from at least three distinct transmission frequencies for each of said transmitters.

27 Claims, 4 Drawing Sheets

METHOD AND APPARATUS FOR REFINABLY ACCURATE LOCALIZATION OF DEVICES AND INSTRUMENTS IN SCATTERING ENVIRONMENTS

FIELD OF THE INVENTION

This invention relates to localization, (the determination of position and/or orientation) of an instrument within a three dimensional region in the presence of external scatterers of electromagnetic fields, and in particular to the localization of a medical device in a patient's body.

BACKGROUND OF THE INVENTION

In the context of medical procedures, it is often necessary to determine the position and/or orientation of a medical device within a patient's body. For example to safely and accurately navigate the distal tip of a catheter through the body, it is desirable to know the position and orientation of the catheter. Standard imaging methods such as x-ray, CT, or MRI may not provide adequate information for use in navigation. Similarly, methods such as image reconstruction and processing, electrical potential measurements, ultrasound and electromagnetic measurements have been used for this purpose. They typically suffer from a lack of sufficient accuracy due to inherent methodological problems, inhomogeneities in the environment, or interference from the environment.

A convenient method for determining position and orientation of a medical device employs the transmission of time-dependent electromagnetic signals between transmitters at a known location and receivers, or vice versa. In the typical situation, a plurality of transmitters are disposed in fixed, known locations, each transmitting at a difference frequency and one or more sensors on the medical device inside the body. From an analysis of the signals received by the receiver coils, sufficient information may be obtained to determine the desired position and/or orientation of the sensor, and thus the medical device relative to known position and orientation of the transmitters. Various examples of such magnetic localization techniques include U.S. Pat. Nos. 5,694,945, 5,846,198, 5,738,096, 5,713,946, 5,833,608, 5,568,809, 5,840,025, 5,729,129, 5,718,241, 5,727,553, 5,391,199, 5,443,489, 5,558,091, 5,480,422, 5,546,951, 5,752,513, 6,092,928, 5,391,199, 5,840,025, U.S. patent application Ser. No. 09/809523, filed Mar. 15, 2001, and published Nov. 29, 2001, as No. 20010045826, and PCT Application No. PC/US01/08389, filed Mar. 16, 2001, and published Sep. 20, 2001, as WO 01/69594 A1, and PCT/GB/01429, published Nov. 16, 2000, as WO 00/68637, the disclosures of all of which are incorporated herein by reference.

The use of time-dependent electromagnetic fields for localization purposes suffers from a significant drawback—in the presence of external electromagnetic scatterers, such as metals, in the environment that can support induced currents, backscatter from these metals can alter the signals received by the receiver coils and lead to significant loss of accuracy in determination of the position and/or orientation. In cases where the external environment is changing, such as moving metals, these changes in signal are not predictable in advance.

SUMMARY OF THE INVENTION

The present invention provides a method of magnetically localizing a device in the presence of external scatterers such as metals. Generally the method of localization of this invention involves transmitting, receiving, and processing magnetic signals so that changing external metallic environments can be accounted for in a refinably accurate manner. In the preferred embodiment, the method employs a plurality of transmitters (e.g. coils) generating electromagnetic signals with at least three distinct frequencies placed at known fixed locations outside a patient's body, and a plurality of sensors (e.g. coils) placed on or within a device or instrument, such as a medical device inserted into a patient's body.

Furthermore, it is necessary that each transmit coil be able to transmit at at least three distinct frequencies. By having each coil transmit at a larger number of distinct frequencies, the accuracy of the localization can be refined successively to the extent desired by suitable processing. The sensors may be any magnetic field sensors such as coils, Hall probes and other devices known to those skilled in the art. The signal processing discards pieces of the signal that arise from external scattering, leaving behind a "true" or desired signal that is, by the use of an increasing number of transmit frequencies, an increasingly accurate approximation to the signal that would be received in a scatter-free environment. This process is convergent and fast, even in a "worst case" situation where the receiver coil and the scatterer are geometrically maximally coupled. Furthermore, the entire process can be carried out in real time, meaning that as long as angular velocities associated with movements of conductors in the environment are significantly smaller than the circular frequencies of the electromagnetic radiation used, changes in environment such as moving metallic equipment are always automatically accounted for. The analysis also provides design methods whereby the accuracy can be further improved.

Thus, the method of this invention provides for accurate and fast localization by electromagnetic means of devices, including but not limited to medical devices, within a three dimensional region such as within a patient's body, which is not significantly affected by the presence of metal near the region of interest.

BRIEF DESCRIPTION OF THE DRAWINGS

Corresponding reference numerals indicate corresponding parts throughout the several views of the drawings.

DETAILED DESCRIPTION OF THE INVENTION

The localization method described herein is based on the use of multiple transmitters (e.g., coils), at least three in number, each fixed at a known spatial location and capable of transmitting electromagnetic radiation at at least three distinct frequencies. Preferably the transmission method uses driving currents in each coil with the time dependence of the currents being sinusoidal at each of the distinct frequencies.

Figure 1:
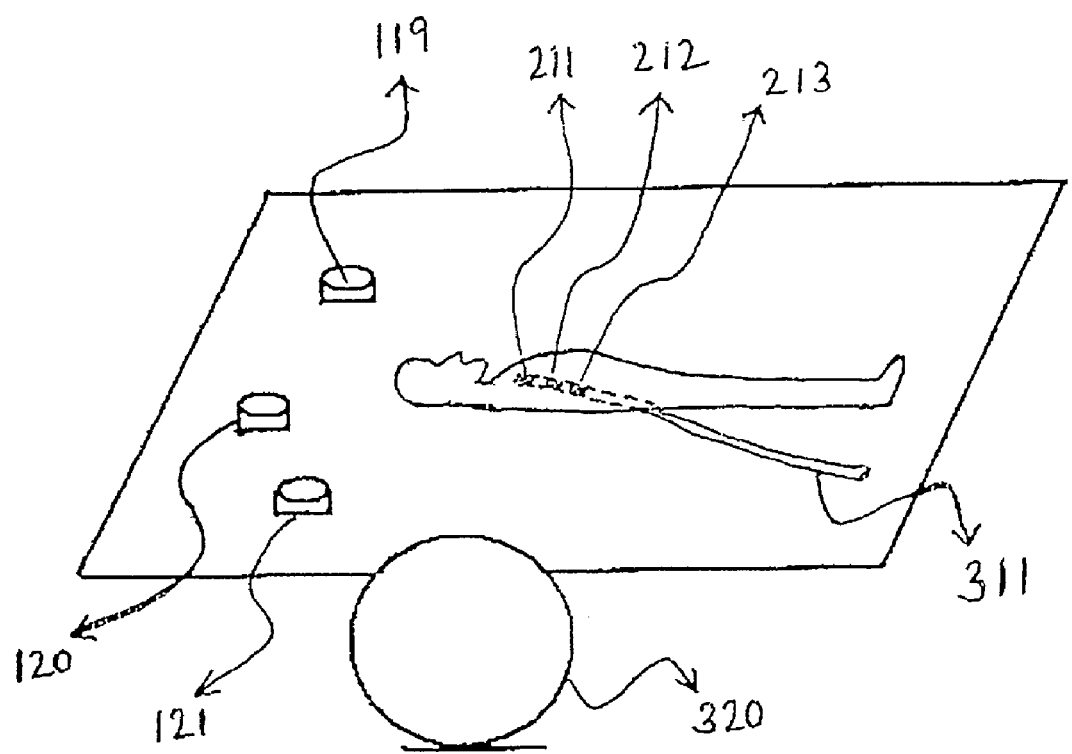
FIG. 1 is a schematic diagram of the general geometry for the case of a medical device (whose position and orientation at the tip is desired) inserted into a patient.

One or more receivers (such as coils or other magnetic field sensor such as Hall probes) is located within or on the device whose localization is desired. While receiver coils are described in this preferred embodiment, it should be understood that this invention includes the use of other magnetic field sensors. An example of a medical device where such coils could be used is a catheter with receiving coils mounted at or near the catheter tip. Due to the time dependence of the transmitted magnetic field, the changing magnetic flux in the receiver coils produces a measurable induced voltage. In the ideal case where external scatterers are absent, localization information may be obtained from an analysis or suitable processing of the induced voltages in the receiver coils. In general external conductors cause interfering signals due to induced currents which produce significant deviations from the ideal case. The general geometry is as shown in FIG. 1, where the transmitter coils 119, 120 and 121 produce changing magnetic fields received by receiver coils 211, 212 and 213, mounted within a catheter 311 introduced into a patient's body 314. The presence of an external conductor such as 320 produces interfering signals in the receiver coils 211, 212 and 213.

Figure 2:
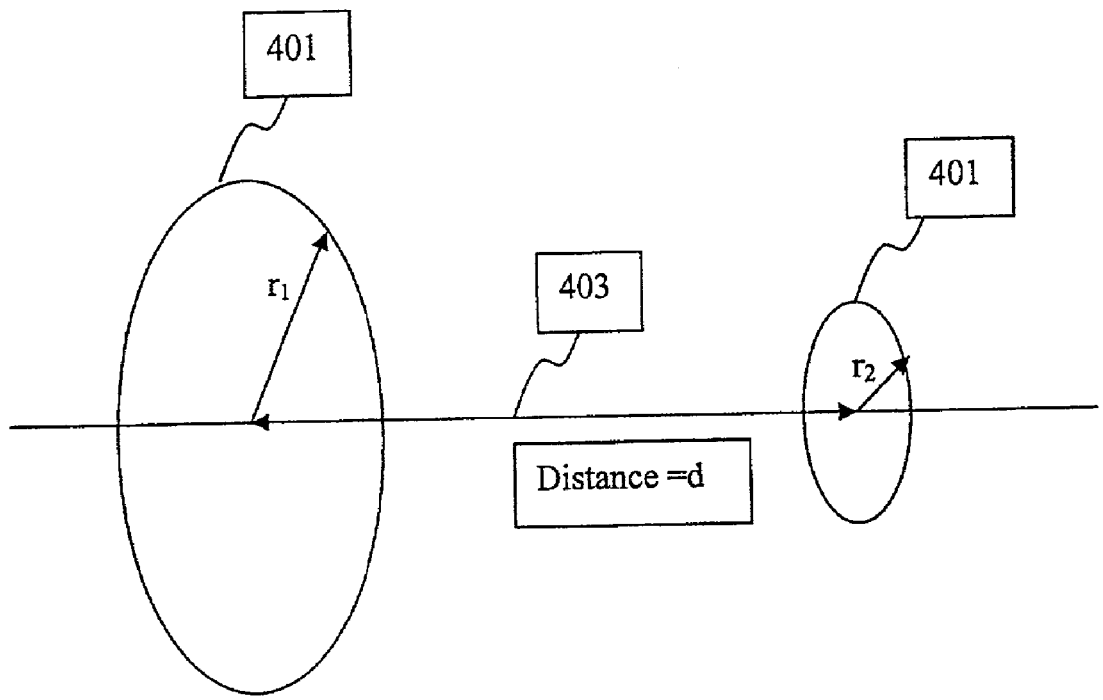
FIG. 2 is a schematic diagram showing the geometry of the "worst case" analysis of the scattering problem.

FIG. 2 illustrates the "worst case" geometry for the receiver coil and external scatterer where the respective magnetic fluxes are maximally linked. As shown in FIG. 2, external scatterer 401 and receiver coil 402 both have circular geometries and share a common axis 403 (referred to herein as the z-axis) so that the planes defined by the respective circles are parallel. The coils are separated by a distance d. The external scatterer 401 has radius $r_1$ and the receiver coil 402 has radius $r_2$. A spatially uniform time-dependent magnetic field along the z-direction, $B(t) = B_0 e^{j\omega t}$, is incident upon the entire geometry. Because other relative orientations and positions of the receiver coil and external scatterer with respect to each other and with respect to the incident field lead to suppression of flux linkage by various trigonometric factors smaller than unity in magnitude, the geometry considered in FIG. 2 is indeed a "worst case" geometry.

As a result of the time-dependent magnetic field, voltages and currents are induced in both receiver coil and external scatterer. The presence of receiver coil and external scatterer in the incident magnetic field scatters the incident field due to induced currents. One way to account for the effect of scattering is as follows. The (time-dependent) induced currents in receiver coil and external scatterer further produce time-dependent secondary magnetic fields which may be considered to act upon each other in an iterative manner. This iterative process is referred to as the Born expansion in the literature (see, for example, J. D. Jackson, Classical Electrodynamics, incorporated herein by reference). For the worst-case geometry shown in FIG. 2, this iterative process can be actually followed through and will be shown to have useful consequences. If $A_1 = \pi r_1^2$ and $A_2 = \pi r_2^2$ are the cross-sectional areas of scatterer and receiver coil respectively, the primary induced voltage in the receiver coil is determined by Faraday's law to be (apart from the complex time-dependent exponential factor)

$$V_2^0 = -B_0 A_2 j\omega \qquad (1)$$

Likewise, the induced voltage in the scatterer is $V_1^0 = -B_0 A_1 j\omega$. If $R_1$ and $R_2$ are the resistances of scatterer and receiver coil respectively, the induced current in the scatterer is $I_1^0 = V_1^0 / R_1$. For the present analysis we will assume that inductive effects are small relative to resistive effects; later this assumption will be relaxed. The magnetic field at the center of the receiver coil produced by the current $I_1^0$ is $$B_1^1 = \mu_0 I_1^0 r_1^2 / 2(d^2 + r_1^2)^{3/2} \qquad (2)$$

where $\mu_0$ is the standard free space magnetic permeability. The field elsewhere in the area defined by the receiver coil is smaller, and so the induced voltage $V_2^1$ in the receiver coil due to the current $I_1^0$ in the scatterer is $$V_2^1 = -B_1 A_2 j\omega \qquad (3)$$

with $B_1$ bounded in magnitude by $|B_1^1|$. Correspondingly there is a current $I_2^1 = V_2^1/R_2$ in the receiver coil. Likewise there is a similar correction $I_1^1$ to the current in the scatterer, and so on.

By a careful examination of this iterative process, it can be shown that the induced voltage in the receiver coil can be expressed as a power series in the frequency:

$$V_2 = V_2^0 + V_2^1 + V_2^2 + V_2^3 + \ldots = -j\omega B_0 A_2 [P - Q](1 - j\beta) \qquad (4)$$

where $$\beta = \pi \omega \mu_0 r_1^4 / 2 R_1 (d^2 + r_1^2)^{3/2} \qquad (5)$$

and P and Q can both be expanded as power series in frequency. In fact, P and Q are bounded from above by $P_1 = 1 + (\alpha^2 + \alpha^4 + \alpha^6 + \ldots)$ and $Q_1 = (\alpha + \alpha^3 + \alpha^5 + \ldots)$ with $$\alpha = (\pi \omega \mu_0)^2 \, r_1^4 r_2^4 / [4 R_1 R_2 (d^2 + r_1^2)^{3/2} (d^2 + r^{22})^{3/2}] \qquad (6)$$

Note that $\alpha$ and $\beta$ are dimensionless parameters. If $\alpha < 1$, P and Q are bounded and finite and so is the series expansion, equation (4), for the induced voltage. The induced voltage in the receiver in the presence of external scattering effects can be expanded in a power series in the frequency as given by equation (4). The coefficients in such an expansion in general depend on the details of the scattering environment.

It is important to note that in the absence of external scatterers, only the first term $V_2^0$ in the expansion (4) above survives, and it is linear in the frequency. This is the primary signal, and non-linear (in frequency) modifications to it arise from scattering effects.

In medical device applications where precise localization is essential, $d \sim 10$ cm, $r_1 \sim 1$ m, $r_2 \sim 2$ cm, $R_1 \sim 1$ ohm, $R_2 \sim 0.1$ ohm are typical representative values. At frequencies of the order of 10 kHz, it can be seen from equation (6) above that $\alpha \sim 0.015$. The series approximation converges rapidly in such cases. At such kilohertz frequencies, low order polynomials can provide excellent approximations to the scattered signal. The linear term (in frequency) in such an approximation then is directly the primary signal and is free of external scattering effects. It must be noted also that the primary voltage signal from the receivers is out of phase with the currents in the transmitter generating the incident radiation.

Low order polynomial (in frequency) fits to the signal may be obtained by a standard method such as least square fitting to the signal obtained at as many distinct frequencies as the order of the desired polynomial fit. The linear term that the polynomial fitting yields is the filtered primary signal. Furthermore, the fit can be refined and improved by collecting the signal at a larger number of distinct frequencies and correspondingly using successively higher order polynomials as required.

While the analysis above applied to the case of thin loops and neglected inductive effects, a more accurate analysis including inductive effects may be performed in a more general case to obtain the induced currents in continuous metal due to time-varying magnetic fields. In this case the induced eddy current density J on the metal may be computed in idealized but representative cases and may be shown to have a convergent expansion in powers of frequency.

Consider the case of a circular metal sheet of radius R and thickness $\delta$, with the metal resistivity being $\rho$. We will suppose for convenience that the thickness $\delta$ is smaller than the skin depth of the metal over the range of frequencies being considered; if not the skin depth (proportional to the square-root of the frequency) should be used in place of $\delta$. If the metal sheet is placed in a sinusoidally time varying and spatially uniform magnetic field perpendicular to the sheet, with amplitude $B_0$ and frequency $\omega$, the induced eddy current density in the sheet depends only on radial distance r from the center of the sheet. The induced eddy currents are circumferential and it can be shown that the current density has a magnitude J(r) given by $$J(r) = (\epsilon B_0 r/2)[1 + (\epsilon \mu_0/2)(R/2 - r(1/3 + 1/24 + \ldots)) + O((\epsilon \mu_0/2)^2) + \ldots] \quad (7)$$

where $\epsilon = -j\omega\delta/\rho$. In particular, it may be shown that this expansion in powers of $\epsilon$ (and thus frequency $\omega$) is convergent. The general scattering signal picked up by the receiver coil then involves sums of products of convergent expansions in powers of frequency and is itself convergent for cases of interest such as those arising in medical applications. The primary scattered signal picked up by the receiver coil is determined by the real part of J in equation (7) and has an expansion in integral powers of frequency.

We now describe a preferred scheme for generating, acquiring and processing electromagnetic signals so as to eliminate scattering effects based on the discussion above. A programmable signal generator is used to generate sinusoidal currents at as many distinct frequencies as the order of the polynomial fit desired. If there are n transmitters, and m (m greater than or equal to n) frequencies, the m frequencies are ordered in magnitude and applied to the transmitters n at a time in circularly permuted fashion, so that each of the m frequencies has been transmitted by each of the n transmitters exactly once. Ordering of frequencies by magnitude is used here only for purposes of discussion. As an example, if there are 3 transmitters A, B and C, and four ordered frequencies (f1, f2, f3, f4), the transmission signal is applied to (A,B,C) in the sequence (f1,f2,f3)-(f2,f3,f4)-(f3,f4,f1)-(f4,f1,f2). The frequencies are chosen to be integrally related such that they are all multiples of a base frequency f0 so that the signal can be frequency multiplexed and easily demodulated upon reception. With such a scheme the signal generator simultaneously uses a superposition or batch of n frequencies at a time, and the m batches are time multiplexed in an entire signal generation cycle. Although this is a preferred scheme for reasons of optimality and efficiency, other signal generation schemes employing signal generation at multiple frequencies would also work, and it is possible to use non-optimal schemes of signal generation and acquisition as well. As an example of a variation on our basic scheme, in the presence of a larger number of transmitters it may be sometimes desirable to use a further level of time multiplexing within each batch of n frequencies.

Figure 3:
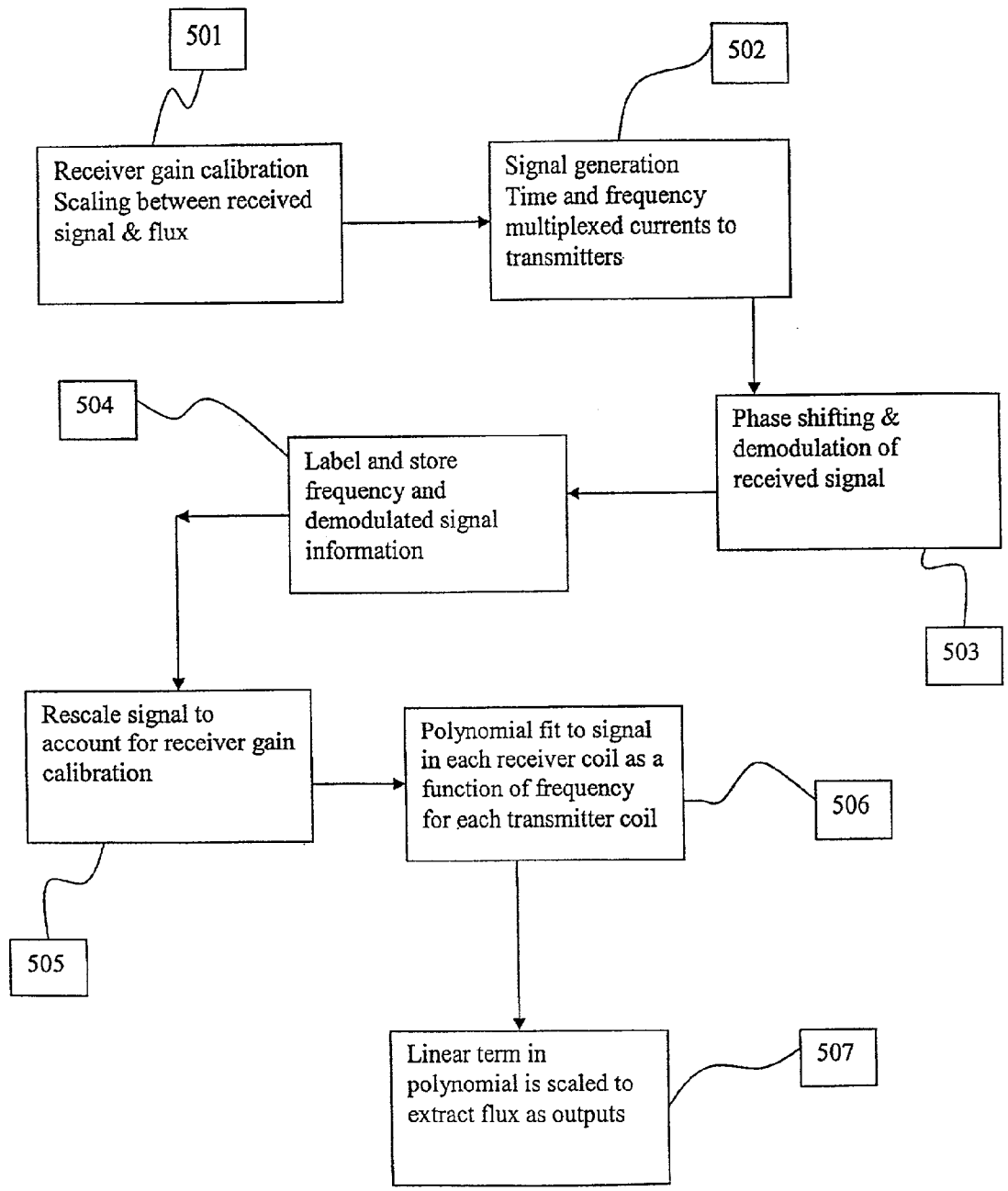
FIG. 3 is a process flow diagram for the preferred embodiment of this invention.

The signals from the receiver from each batch of frequency multiplexed signals can be easily demodulated given the choice of integral relationships among the frequencies mentioned above. A microprocessor-based controller is used to keep track of the frequency and signal obtained from each of the n transmitters in each of the m batches of multiplexed frequencies. At the end of the m batches, the received signal for each of the m frequencies is available for each of the n transmitters. FIG. 3 shows a process flow chart illustrating the method.

Referring to FIG. 3, in step 501 the receiver gain is calibrated as a function of frequency to account for any frequency-dependent gain changes in the signal reception circuitry. In this step the scaling between received voltage signal and measured flux amplitude is also calibrated at fixed frequencies using known fluxes. Additionally the transmitter drive currents are calibrated as a function of frequency. Although it is most convenient to hold the transmitter currents fixed as frequency varies, in some cases it may be advantageous to allow the transmitter currents to vary with frequency, and in this case it is necessary to calibrate this variation. The signal generation step 502 produces in time multiplexed fashion m frequency multiplexed batches of n frequencies as sinusoidal superpositions. For each of the m batches of transmitted signal, the received signal is phase shifted by $\pi/2$ (since the primary signal we are interested in is out of phase with the transmitted signal) and demodulated in step 503 in order to separate the signals received from distinct transmitters. This information is labeled and stored in step 504. In step 505, the calibration performed in step 501 is used to rescale the signals at various frequencies stored in step 504, if appropriate and the rescaled signals are stored. In step 506, an m-th order polynomial fit is used to determine the coefficients in a polynomial expansion (in powers of frequency) of the rescaled signals obtained in step 505. In step 507, the coefficient $c_1$ of the linear term obtained from step 506 is used (so $c_1\omega$ is the free-space or metal-free signal) together with the scaling between signal and flux to obtain the flux from each transmitter. It is to be noted that steps 504 through 507 may also be performed on a computer connected to the microprocessor.

If there is more than one receiver, steps 501 through 507 are performed for each receiver. It is optimal to perform this series of steps as a parallel process for the various received signals from each receiver although this could be performed in serial fashion. From the various fluxes it is possible to determine the required position and orientation of the device by a variety of computational methods not addressed herein.

Figure 4:
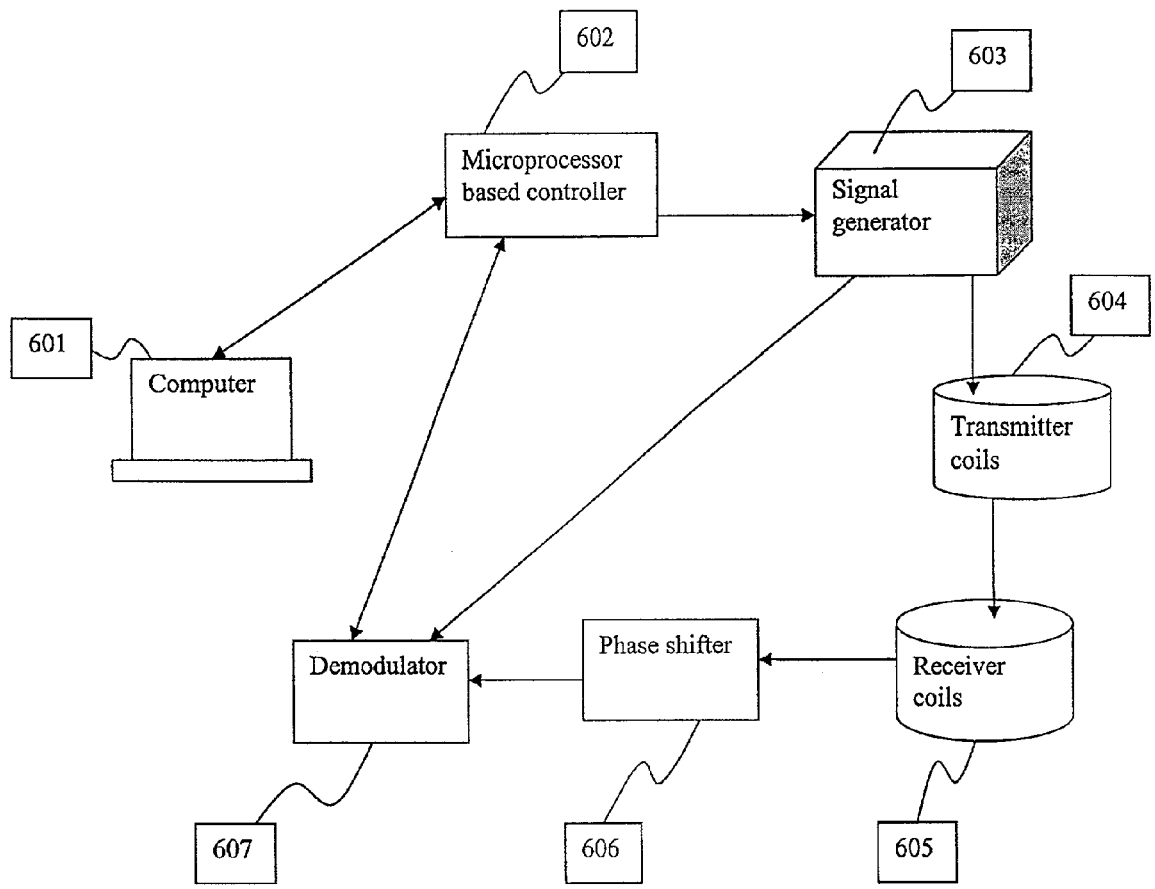
FIG. 4 is a system diagram of a system that implements the method of the invention.

FIG. 4 shows a system diagram for a preferred embodiment of the invention. A programmable interface preferably on a computer 601 is used to program the order of the polynomial fit desired. A microprocessor-based controller 602 uses this information to pick a sequence of transmission frequencies. The signal generator 603 applies the desired currents in frequency multiplexed batches to the transmitters 604 in a time multiplexed fashion as outlined in FIG. 3 and explained in the description above. The signals from the receivers 605 are phase shifted by a phase shifter 606 and demodulated by the signal demodulator 607. The signals are stored in the microprocessor-based controller 602 and buffered to the computer 601 together with associated frequency information and receiver labels. Previously stored calibrations in the computer 601 account for variations in signal gain with frequency and a suitable correction is applied to the buffered signals to obtain rescaled signals. The computer 601 then performs, for each receiver, a polynomial fit at the chosen order of fit and extracts the coefficient of the linear term in the polynomial expansion corresponding to the transmission from each transmissitter. This set of coefficients is rescaled based on information previously stored in the computer 601 in order to obtain a corresponding set of fluxes. The set of fluxes is suitably processed in the computer 601 to obtain position and orientation information which is available as system output.

The above system description is a preferred embodiment and variations depending for instance on convenience of application are possible as may be familiar to those skilled in the art. For example, it may sometimes be desirable to perform more of the information processing within the microprocessor-based controller.

The range of frequencies employed may range from 100 Hz to 40,000 Hz and more preferably from 500 Hz to 15,000 Hz. From equation (6), it may be seen that a method to improve the accuracy of the fit and lower the order of polynomial required is provided by increasing receiver resistance ($R_2$). The use of higher resistance metal elements or alloys (as compared to commonly used copper conductors) in the receiver construction is particularly indicated. So also is receiver size or total area of flux-capturing cross section, although this trades off with lower reception voltage levels.

What is claimed is:

1. A method of localizing a device, medical or otherwise, within a three dimensional environment, the method comprising: (a) transmitting time varying magnetic fields from at least three transmitters, (b) receiving the transmitted electromagnetic radiation as induced voltage signals from at least one receiver mounted on or within said device, and (c) processing said received voltage signals in order to extract position and orientation localization information for said device, said processing including phase-shifting and correction for conducting materials in the vicinity by the use of information gathered from fitting said phase-shifted induced voltage signals with polynomial functions having terms in powers of frequency using at least three distinct transmission frequencies for each of said transmitters.

2. The method according to claim 1 wherein the at least one receiver is a coil.

3. The method according to claim 1 wherein the at least one receive is a magnetic field sensor.

4. The method of claim 1, where the distinct transmitters emit electromagnetic radiation at different frequencies in frequency multiplexed form.

5. The method of claim 1, where the transmitters emit electromagnetic radiation as a transmission cycle of time multiplexed batches, each said batch comprising frequency modulated signals.

6. The method of claim 5, where said transmission cycle is repeated and averaged so as to increase signal to noise ratio.

7. The method of claim 5, where said transmission cycle includes the use of batches of multiplexed frequencies and further time multiplexing the batches in successively circularly permuted sequence of frequencies, said time multiplexed batches being equal in number to the total number of distinct frequencies employed, so that each frequency is transmitted by each transmitter in exactly one batch of each said transmission cycle.

8. The method of claim 7, where said transmission cycle generation is controlled by a microprocessor-based controller.

9. The method of claim 1, where the total number of transmission frequencies equals or exceeds the number of transmitters.

10. The method of claim 5, where the generation of currents driving said transmission cycle is controlled by a microprocessor-based controller.

11. A method for processing signals received by a receiver at multiple frequencies from each of a number of transmitters, where said processing includes, for each pair of receiver and transmitter: (a) producing polynomial fits of given order to the signal as a function of frequency, (b) said polynomial fit produced by a fitting procedure, weighted or otherwise, that in the case of a weighted procedure may employ different weights for different frequencies in order to improve the fit over desired frequency ranges, and (c) extracting the coefficient of the linear term in the polynomial fit as the flux in the receiver produced by each said transmitter.

12. The method of claim 11, where said given order of polynomial is fixed electronically by construction.

13. The method of claim 11, where said given order of polynomial is programmable by a user by means of electronic or other input.

14. The method of claim 11, where said processing may be refined by picking higher orders for the polynomial fit by means of an automated system which checks for a measure of goodness of fit.

15. A system for generating, acquiring and processing signals for the purpose of localizing position and orientation of a device in three dimensional space by electromagnetic means, said system comprising: (a) a main computer and programmable interface for refining the accuracy of localization estimation by signal generation, acquisition and processing, (b) a microprocessor controlled signal generation system linked to said main computer, (c) a set of at least three transmitters located at known fixed locations and orientations in three dimensional space, (d) at least one receiver mounted on or within the device at which location position and orientation is desired to be found, said transmitters configured to be driven by said signal generation system at a plurality of frequencies in time and frequency multiplexed fashion to induce voltage signals in the at least one receiver, and (e) processing software for producing polynomial fits to phase-shifted induced voltage signals in powers of frequency using at least three of said frequencies to provide at least three polynomial coefficients for use in correcting the voltage signals for conducting materials present in the surrounding three dimensional space.

16. The system according to at least claim 15 wherein the at least one receiver is a coil.

17. The system of claim 16, where area of flux-capturing cross section of said receiver coil is made small enough to reduce secondary scattering effects.

18. The receiver coil of claim 16, where the material of construction for said receiver coil may incorporate metals, conducting metallic alloys or non-metallic conductors whose resistance is higher than that of copper.

19. The system according to claim 15 wherein the at least one receiver is a magnetic field sensor.

20. The system of claim 15 where said processing software is implemented in the main computer.

21. The system of claim 15 where said processing software is implemented in the microprocessor-based controller.

22. The system of claim 15 where said microprocessor-based controller is programmed from and controlled by said main computer.

23. The method of claim 15, where said processing software includes a means of refining the localization estimate by picking higher orders for the polynomial fit by means of an automated system which checks for a measure of goodness of fit.

24. A method of localizing a medical device within a three-dimensional environment, the method comprising:

transmitting time varying magnetic fields at at least three frequencies from each of at least three transmitters;

receiving electromagnetic radiation of the transmitted fields as an induced voltage signal from at least one receiver of the device;

phase-shifting the induced voltage signal; curve-fitting the phase-shifted induced voltage signal as a function of frequency to obtain a polynomial expansion in powers of frequency;

using the linear term coefficient of the polynomial expansion to determine a flux induced in the at least one receiver from each transmitter; and using the fluxes to determine a position and orientation of the device.

25. A method of localizing a medical device within a three-dimensional environment, the device including at least one receiver that can receive signals from at least three transmitters in the environment, the method comprising:

selecting an order of polynomial fit;

selecting a plurality of transmission frequencies based on the selected order;

driving the transmitters to transmit signals at the selected frequencies in frequency-multiplexed batches;

for each of the at least one receiver:

receiving voltage signals induced in the receiver by the transmitted signals;

curve-fitting at the selected order of fit to components of the voltage signals as a function of frequency to obtain for each receiver at least one polynomial expansion in powers of frequency;

extracting a linear term coefficient from each of the polynomial expansions; and using the coefficients to correct device localization for conducting material in the environment.

26. The method of claim 25 wherein driving the transmitters comprises allowing transmitter currents to vary with the selected frequencies.

27. An apparatus for processing a signal received by a receiver mounted on or within a medical device at a plurality of frequencies from each of a plurality of transmitters, the apparatus comprising, for each pair of the receiver and one of the transmitters:

means for producing polynomial fits to the signal as a function of frequency, wherein the polynomial fit production means employs different weights for different frequencies to improve the fits over desired frequency ranges; and means for extracting a coefficient of a linear term of each of the polynomial fits to determine flux in the receiver produced by each said transmitter.

* * * * *